United States Patent [19]

Eaton

[11] Patent Number: 5,062,310
[45] Date of Patent: Nov. 5, 1991

[54] PROBE INLET APPARATUS AND METHOD

[75] Inventor: David K. Eaton, Austin, Tex.

[73] Assignee: Jade Systems, Inc., Austin, Tex.

[21] Appl. No.: 487,599

[22] Filed: Mar. 1, 1990

[51] Int. Cl.$^5$ ............................................. G01M 19/00
[52] U.S. Cl. ..................................... 73/866.5; 277/80
[58] Field of Search ............. 73/866.5, 863.85, 863.86, 73/864.85, 23.41, 864.86, 864.87; 277/80

[56] References Cited

U.S. PATENT DOCUMENTS

| 3,043,303 | 2/1962 | Still | 73/863.86 X |
| 4,056,981 | 11/1971 | Kalka et al. | 73/863.85 |
| 4,359,908 | 11/1982 | Perces | 73/863.85 |
| 4,476,732 | 10/1984 | Karg | 73/863.73 |
| 4,682,508 | 7/1987 | Steiner et al. | 73/863.85 X |
| 4,854,181 | 8/1989 | Gerstel | 73/863.86 |

FOREIGN PATENT DOCUMENTS 3400458 4/1987 Fed. Rep. of Germany .

Primary Examiner—Tom Noland
Attorney, Agent, or Firm—Shaffer & Culbertson

[57] ABSTRACT

A probe inlet apparatus comprises an annular seal member and an inner seal device both mounted within an inlet housing having an inlet housing cavity extending therethrough. The inner seal device comprises a seat member connected to the inlet housing and a seal member ball adapted to seat against a seat member opening to form an inner seal. The seal member is responsive to a magnetic seal member positioning force produced by a suitable magnetic associated with the inlet housing to be held in the seated position so as to form the inner seal. An elongated probe may be inserted through the inlet housing cavity to first form an annular seal with the annular seal member and then to contact and displace the seal member against the magnetic positioning force from its seated position to an unseated position allowing the probe member to reach a desired probe depth. As the probe member is withdrawn from the inlet housing, the magnetic seal member positioning force moves the seal member back to the seated position to reestablish the inner seal before the probe is removed from the annular seal member to break the annular seal.

21 Claims, 3 Drawing Sheets

PROBE INLET APPARATUS AND METHOD

BACKGROUND OF THE INVENTION

This invention relates to devices for maintaining a substantial seal to an isolated environment while allowing the introduction and withdrawal of a probe member. The invention relates particularly to a probe inlet device and method for facilitating the introduction of a sample onto a chromatography column.

A number of procedures, particularly chemical testing procedures, require the introduction of a probe member into an isolated environment for injecting or extracting a sample of the material. For example, chromatography involves introducing a sample of material onto a column through which a liquid or gas eluent or mobile phase is passed. The column is composed of a second or stationary phase which may be a solid or liquid onto or into which the sample may be absorbed or dissolved.

In gas chromatography, where the mobile phase is a gas and the stationary phase is either a liquid or solid, the sample was commonly introduced through a septum with a suitable syringe. The syringe needle was adapted to penetrate completely through the septum so that the sample could be injected into a sample introduction area at one end of the column. The septum material formed a seal around the syringe needle while the needle was inserted and then closed up the puncture hole and formed a seal once the syringe needle was withdrawn.

There were several problems associated with the use of septums in introducing a probe into an isolated environment. One such problem was that the septum material was damaged after repeated injections leading to leaks through the material which allowed material to escape from the isolated environment. Such leakage resulted in altered readings in the case of chromatographic devices. The leaks also allowed oxygen from the atmosphere to enter the isolated environment. In chromatography such oxygen leakage damaged the stationary phase and altered its performance. The septum material also commonly contained elastomeric polymers which degraded when exposed to elevated temperatures. Such degradation released foreign material from the septum into the isolated environment. In chromatography, this release of vaporized material from the septum was referred to as septum bleed and was undesirable in that the released material often damaged the column material or altered the response of the instrument detectors. Septum bleed was also accompanied by loss of elasticity in the septum material which resulted in decreased ability of the septum material to seal the hole caused by the needle insertion, and reduced the lifetime of the septum.

U.S. Pat. No. 4,854,181 and German Patent No. 34 00 458 both to Gerstel show septumless sample injection and extraction devices specifically adapted for use in gas chromatography. Both devices include a valve body having an annular outer seal and an inner seal that includes a sealing member adapted to be thrust obliquely out of a sealing position by contact with an injection or extraction probe as the probe is inserted through the valve body. The seal member is a ball adapted to seat in a sealing ring in the German patent and an elongated sealing member adapted to seal against an O-ring in the U.S. patent. In both devices, a spring mechanism is used to hold the sealing member in the sealing position when the probe is not inserted through the housing and to return the sealing member to the sealing position as the probe is withdrawn.

Although the Gerstel devices avoid some of the leakage problems associated with septum-type sample injection and extraction arrangements, there were still several problems associated with such septumless devices. Both Gerstel devices required elastomeric O-ring seal members in the inner seal arrangement. These O-rings were made of materials that broke down at high temperatures so a to lose their elasticity and ability to seal. The O-ring material breakdown also released foreign material into the chromatography column. Furthermore, both Gerstel devices required the probe member to contact the particular seal member at an angle and provide a substantial lateral force to unseat the seal member. Such lateral force damaged the relatively fragile probe members, particularly probe members used in automated samplers which inject the probe member rapidly.

It is therefore an object of the invention to provide a probe inlet apparatus for facilitating the introduction and withdrawal of an elongated probe member that overcomes the abovedescribed problems and others associated with probe inlet devices. It is also an object of the invention to provide a method for introducing a probe into an isolated environment while maintaining a substantial seal to the isolated environment.

SUMMARY OF THE INVENTION

A probe inlet apparatus according to the invention includes annular seal means and an inner seal both contained within an inlet housing. The inner seal is formed by a seal member adapted to be positioned over a seat opening of an inner seal seat member in response to a magnetic positioning force produced by suitable means associated with the inlet housing. The annular seal means is adapted to form a seal about the body of an elongated probe as the probe is inserted through the housing from the annular seal toward the inner seal. With the annular seal formed about the probe body, the probe may be inserted through the seat opening to contact and move the seal member to an unseated position to allow the probe member to pass completely through the inlet device. When the probe is withdrawn from the seat opening, the magnetic positioning force moves the seal member back to its seated position so that the inner seal may be reestablished in response to a pressure differential across the seat member forcing the seal member against the seat material.

Unlike the mechanical biasing springs used in prior probe inlet devices which require continuously greater unseating force as the biasing spring is compressed, the magnetic positioning force remains relatively constant or decreases somewhat as the seal member is moved to the unseated position. Furthermore, the magnetic positioning force allows for substantially on-axis contact between the probe and the seal member to initially unseat the seal member with substantially no lateral force on the probe. This lack of a lateral force on initial contact lessens the possibility of probe damage, particularly where automated probe insertion devices are used.

The probe inlet apparatus according to the invention also substantially eliminates the need for elastomeric seals that are continuously exposed to the isolated environment and pose the risk of elastomer bleed at elevated temperatures. The annular seal means of the invention is exposed to the isolated environment only when the inner seal is broken during probe insertion and, therefore, is substantially protected from the isolated environment. Also, the inner seal according to the invention requires no elements that degrade at gas chromatograph operating temperatures.

The preferred magnetic positioning force is provided by a permanent magnet positioned within the inlet housing between the annular seal means and the inner seal. The magnet is generally tubular in shape with a longitudinal opening aligned with the annular seal means and inner seal for enabling the probe member to pass completely through the inlet housing. With the magnet positioned between the annular seal means and the inner seal, the positioning force applied to the seal member is at a maximum when the seal member is in the seated position and somewhat less when in the unseated position. The reduced force applied to the seal member when it is in the unseated position reduces the lateral force applied to the probe as it extends past the inner seat member opening and further reduces the danger of probe damage resulting from insertion.

The annular seal means preferably includes an annular seal member sealed by suitable means in an outer end of the inlet housing and having an opening extending therethrough adapted to tightly receive the elongated probe member to form the desired annular seal. The annular seal member preferably includes an annular seal member body adapted to be received within the inlet housing and a positioning flange adapted to abut the outer end of the housing. A retainer member is adapted to connect to the inlet housing over the outer end thereof and the positioning flange to compress the flange and form the seal between the housing and the annular seal member. This preferred sealing arrangement reduces stress on the annular seal body in a direction transverse to the opening therethrough which could distort the opening and interfere with the annular seal around the probe member body.

The preferred probe inlet apparatus also includes seal member guide means for guiding the seal member, preferably a spherical member, from the unseated to the seated position as the elongated probe is withdrawn from the housing. The seal member guide means in one form of the invention comprises a frusto-conical surface formed within the inlet housing and positioned with its smaller diameter end generally adjacent to the inner seal seat member and with the larger diameter opening extending away from the inner seal seat member toward an inner end of the inlet housing. In this form of the invention, the seal member is not restrained to one particular unseated position and may roll off to any side of the probe member as the probe member is inserted through the seat opening. As the probe member is withdrawn from the seat opening the frustoconical guide surface guides the seal member back to the seated position against the seat member at the smaller end of the frustoconical shape.

A container member is preferably positioned over the larger diameter end of the frustoconical seal member guide to form a seal member chamber for containing the seal member even in the absence of the magnetic positioning force. The container member includes an opening aligned with the annular seal and inner seal seat member opening that is large enough to allow the probe member to pass but small enough to prevent the escape of the seal member from the device.

The preferred form of the invention also includes offsetting means for contacting the seal member after it is unseated by the probe member so as to offset or displace the seal member to the side of the probe member. The offsetting means preferably includes an offsetting ball that is substantially identical to the sealing member ball. Alternatively, an offsetting member connected to the inlet housing within the seal member chamber may provide the desired seal member offsetting action.

The method of the invention includes retaining the seal member over the seat member opening with the magnetic seal member positioning force to form the inner seal, and then inserting the elongated probe through the annular seal to form a substantially sealed chamber between the annular seal and the inner seal. Once the annular seal is formed the method continues with the step of inserting the elongated probe member through the inner seal seat opening to contact and unseat the seal member so that the probe may be inserted even further to a sample injection or extraction point. The annular seal around the probe member body prevents the leakage of material through the inlet housing when the inner seal is broken and the seal member is in the unseated position.

Once the desired sample is injected or extracted, the method continues with the step of withdrawing the probe from the seat member opening while maintaining the annular seal, and then positioning the seal member over the seat opening with the magnetic positioning force so that the inner seal may be reestablished. With the inner seal reestablished, the method concludes with the step of withdrawing the probe completely from the annular seal.

The preferred method of the invention also includes the steps of offsetting or displacing the seal member transversely to the probe axis as the probe is inserted through the device and guiding the seal member from the unseated to seated position as the probe member is withdrawn with a guide surface formed within the inlet housing. In one form of the invention, the guide comprises the frustoconical surface formed in the inlet housing, and the offsetting or displacing step includes contacting the seal member with an offsetting member contained within the area of the frustoconical shape. This offsetting step helps ensure that the seal member does not interfere with the injecting or extracting functions of the probe.

These and other objects, advantages, and features of the invention will be apparent from the following description of the preferred embodiments, considered along with the accompanying drawings.

DESCRIPTION OF THE PREFERRED EMBODIMENTS

Figure 1:
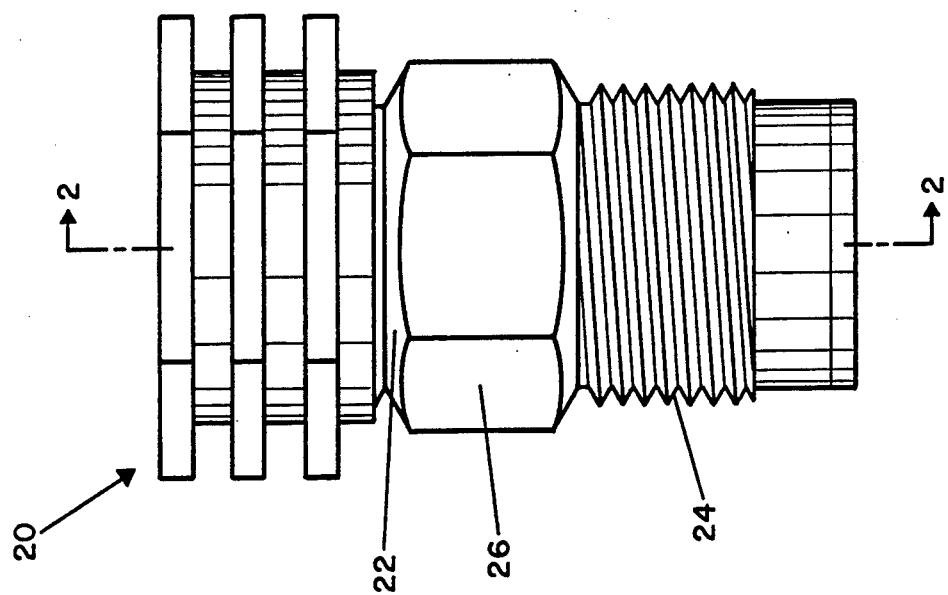
FIG. 1 is a view in side elevation of a probe inlet apparatus embodying the principles of the invention.

FIGS. 1 through 5 illustrate the preferred form of a probe inlet apparatus 20 embodying the principles of the invention. Referring particularly to FIG. 1, the probe inlet apparatus 20 includes an inlet housing 22 made of suitable material having a connector 24 at an inner end thereof for connecting the apparatus to a vessel or container (not shown) containing an isolated environment. The preferred connector 24 includes a male thread formed on the inner end of the inlet housing. The exterior surface of the inlet housing 22 also includes a hexagonal or other suitable surface 26 by which the housing may be gripped to make up the threaded connector 24 in a corresponding female threaded connector (not shown).

Figure 2:
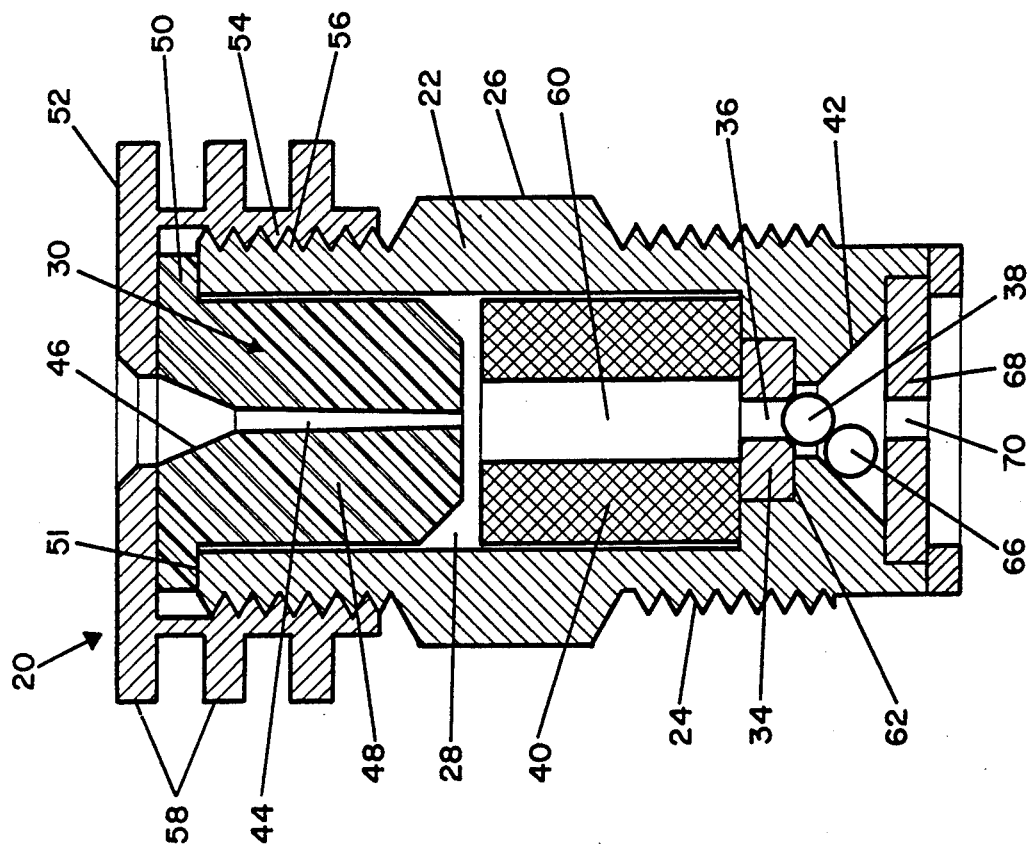
FIG. 2 is a somewhat enlarged view in longitudinal section taken along line 2—2 in FIG. 1.

As shown in FIG. 2, the inlet housing 22 includes an inlet housing cavity 28 extending longitudinally therethrough. An annular seal member generally indicated at reference number 30 is connected to the inlet housing 22 at an outer end thereof and an inner seal is formed toward an inner end of the housing from the annular seal member. The inner seal comprises an inner seal seat member 34 having a seat member opening 36, and a seal member 38 adapted to seat over the seat member opening in a sealing arrangement. Seal member positioning means, in this case comprising a permanent magnet 40 mounted within the inlet housing 22, provides a magnetic seal member positioning force for positioning the seal member 38. The preferred housing 22 shown in FIG. 2 also includes seal member guide means comprising a generally frustoconical surface 42 formed within the inlet housing.

The annular seal member 30 is formed from a suitable elastomeric material such as PTFE polymer or polyimide polymer and includes an annular seal opening 44 with a conically shaped probe guide section 46, an annular seal member body 48, and a positioning flange 50. The annular seal member body 48 is adapted to be received in the inlet housing cavity 28 of the inlet housing 22 with the positioning flange 50 abutting an outer end surface 51 of the housing. An annular seal member retainer 52 having heat dissipating ridges 58 is adapted to seal and retain the seal member 30 within the inlet housing by the positioning flange 50. The annular seal member retainer 52 preferably includes a female threaded portion 54 adapted to connect with a corresponding male threaded portion 56 on the inlet housing so as to compress the flange portion 50 against the outer end surface 51 to form a secure seal with the housing 22. Substantially all of the compression to form the seal with the housing 22 is parallel to the longitudinal axis of the annular seal opening 44 so that the seal with the housing does not substantially interfere with the shape or size of the annular seal opening.

In the illustrated preferred form of the invention, the magnet 40 is positioned within the inlet housing 22 between the annular seal member 30 and the inner seal seat member 34. To allow probe members (FIGS. 3-5) to pass through housing 22, the permanent magnet 40 is generally tube-shaped and includes a magnet opening 60 aligned with the annular seal opening 44 and the seat member opening 36 within the inlet housing 22. Although the magnet 40 is preferably a permanent magnet, alternative forms of the invention could employ an electromagnet for providing the desired magnetic seal member positioning force.

The inner seal seat member 34 preferably includes a separate seat member ring formed of a suitable seat material such as synthetic sapphire, and is adapted to be received in a seat member groove 62 machined or otherwise formed within the inlet housing 22. The seal member 38 in the preferred form of the invention comprises a sealing ball adapted to seat in the seat member 34 over the seat member opening 36. The seal member ball 38 is preferably made of a hard paramagnetic material such as a tungsten carbide/cobalt composite adapted to be held securely in the seated position over the seat member opening 36 in response to the magnetic positioning force produced by the magnet 40.

Referring still to FIG. 2, the frustoconical surface 42, which forms the preferred seal member guide means, is integrally formed within the inlet housing 22 with the smaller diameter opening generally adjacent to the seat member 34 and with the larger diameter opening extending away from the seat member 34 toward the inner end of the inlet housing. A seal member container member 68 is preferably connected over the larger diameter end of the frustoconical shape 42 to form a ball or seal member container chamber defined generally by the area of the frustoconical shape. The seal member container member 68 includes an opening 70 generally aligned with the annular seal member opening 44, the magnet opening 60, and the seat member opening 36 and is adapted to allow an elongated probe member (FIGS. 3-5) to pass therethrough while preventing the larger diameter ball or seal member 38 from escaping from the container chamber.

The preferred form of the invention illustrated in FIG. 2 also includes offsetting means for offsetting or displacing the seal member 38 transversely with respect to the inlet housing cavity longitudinal axis as the probe member (FIGS. 3-5) is inserted through the housing 22. The offsetting means in FIG. 2 comprises an offsetting ball 66 that is substantially identical to the seal member ball 38.

Figure 3:
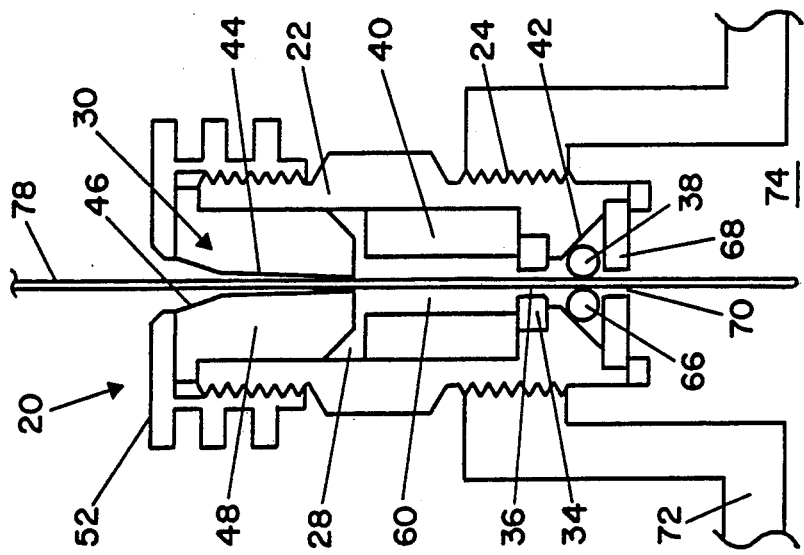
FIGS. 3 through 5 are representational views in longitudinal section similar to FIG. 2 showing sequentially the operation of the probe inlet apparatus according to the invention.
Figure 4:
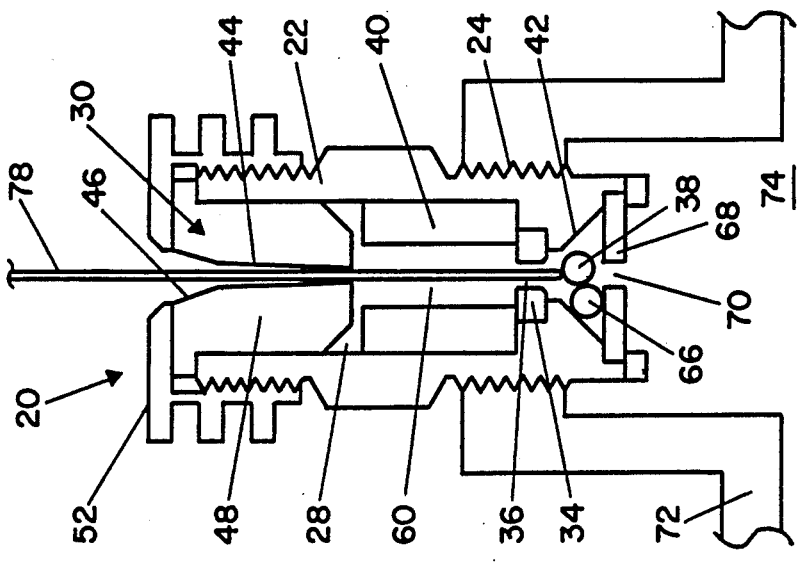
Figure 5:
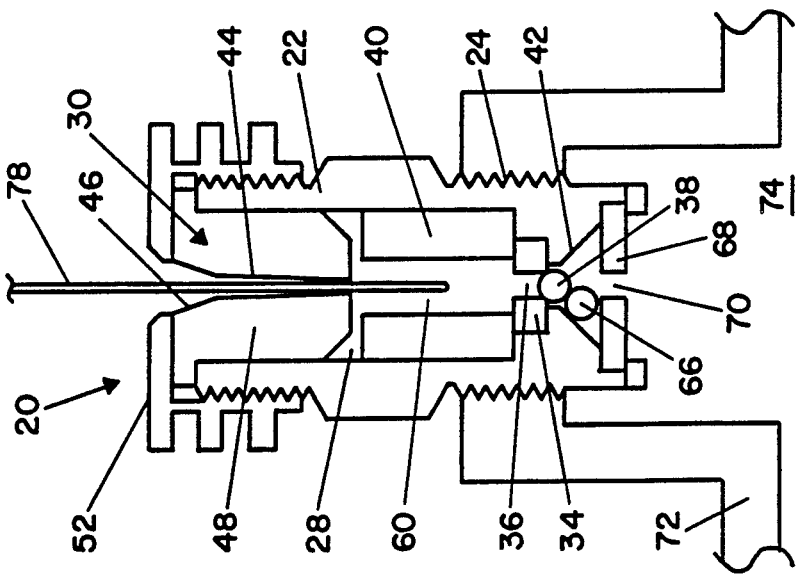

The method and operation of the invention may be described with particular reference to FIGS. 3-5 which each show a probe inlet apparatus 20 similar to that shown in FIG. 2, but connected by the male connector thread 24 to a vessel or container 72 containing an isolated environment generally indicated at reference number 74. The method includes first retaining the seal member or ball 38 in the seat member 34 over the seat member opening 36 to form an inner seal as shown in FIG. 2. This inner seal provides a substantially continuous seal to the isolated environment 74 without the use of any elastomeric sealing elements which may degrade at elevated temperatures to lose elasticity and release foreign material into the isolated environment.

With the inner seal formed, the method of the invention continues with the step of inserting the forward end of an elongated probe member 78 through the annular seal opening 44 of the annular seal member 30 as shown in FIG. 3. The step of inserting the probe 78 through the annular seal opening 44 produces a substantially sealed chamber between the inner seal and the annular seal formed by the annular seal member body 48 around the probe member 78.

After inserting the probe member 78 to form the annular seal around the probe member, the method includes inserting the probe member through the seat member opening 36 of the seat member 34 to contact and unseat the seal member or ball 38 as shown in FIG. 4. As the probe member 78 extends further through the seat member opening 36, the seal member 38 is rolled to one side of the probe along the guide surface 42 to an unseated position shown in FIG. 5 that allows the probe to pass through the ball container member opening 70 to a desired probe depth. Once at the desired probe depth, the desired sample extraction or injection operation may be performed through the probe member 78.

After completing the desired probe operation, the method continues with the step of withdrawing the probe member 78 from the seat opening 36 and positioning the seal member or ball 38 back over the seat member opening 36 with the magnetic positioning force in position to reestablish the inner seal and return the apparatus to the state shown in FIG. 3. The preferred guide surface 42 guides the seal member 38 back to the seated position under the magnetic positioning force produced by the magnet 40. With the inner seal reestablished to seal the isolated environment 74, the elongated probe member 78 is finally withdrawn from the annular seal member 30 and the inlet housing 22 to return the apparatus to the condition shown in FIG. 2.

As indicated above, in the entire interval in which the inner seal is broken and the seal member 38 is moved to the unseated position (FIG. 5), the annular seal formed between the probe member 78 and the annular seal member 30 isolates and maintains a seal to the environment 74 within the vessel 72. Although the annular seal member body 48 may contain elastomers, exposure to the isolated environment 74 is limited to the time in which the probe 78 is inserted through the inner seal. This elastomer exposure time is very small in comparison to the time when the inner seal is formed, and during the time the inner seal is formed, the seal member 38 prevents any material released from the annular seal member material from entering the isolated environment 74. Furthermore, the heat dissipating ridges 58 on the preferred annular seal member retainer 52 help to cool the annular seal member material to reduce the release of material.

Referring particularly to FIG. 4, the method of the invention also preferably includes offsetting or displacing the seal member or ball 38 with the offsetting ball 66. As the probe member 78 unseats the seal member ball 38, it pushes both the seal member ball and the offsetting ball 66 downwardly until the offsetting ball 66 contacts the container member 68. Prior to this point, the probe member 78 contacts the seal member ball 38 substantially on-axis and at a surface substantially perpendicular to the probe longitudinal axis. However, once the offsetting ball 66 contacts the container member 68, the offsetting ball serves to move the seal member ball 38 to the right in the drawing as the probe member 78 is inserted further. Eventually the probe member 78 passes between the balls 38 and 66 as shown in FIG. 5. Since the balls 38 and 66 are identical, either one may reestablish the inner seal upon removal of the probe member 78.

In addition to offsetting the seal member 38 as the probe member 78 is inserted, the preferred offsetting ball 66 also serves as a dampening means for dampening the movement of the seal member upon removal of the probe member. When the probe member 78 is withdrawn from the seat member opening 36, movement of the fluid in the isolated environment 74 may cause the seal member 38 to swirl around in the frustoconical area momentarily before being returned to the seat member 34 by the magnetic positioning force. However, the offsetting ball 66 contacts the seal member 38 to help dampen any swirling movement. This dampening allows the magnetic positioning force to return the seal member 38 to the seated position more quickly.

Figure 6:
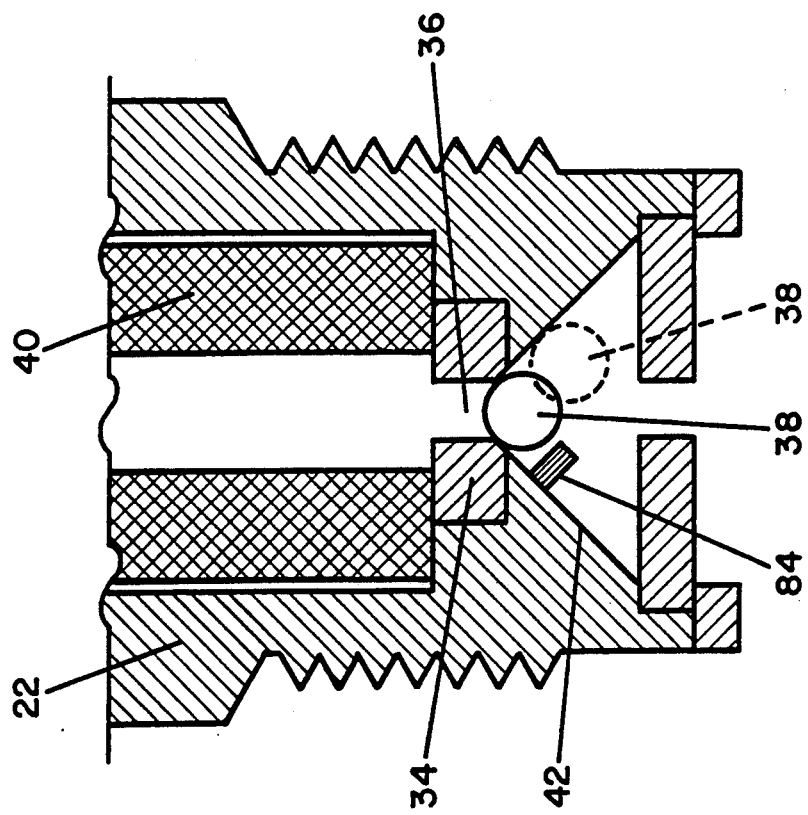
FIG. 6 is a partial section view of an alternate seal member guide according to the invention including an offsetting member.

Other forms of the invention may include alternate offsetting means for cooperating with the probe member to displace the seal member or ball 38 in a transverse direction to the probe axis as the probe is inserted through the seat member opening 36. FIG. 6 shows one alternate form of offsetting means according to the invention. The alternate offsetting means includes an offset member or pin 84 adapted to contact the seal member 38 after it is unseated by a probe member similar to the probe member 78 in FIGS. 3-5 to provide a transverse offsetting force as the probe member is inserted through the seat member opening 36. The offsetting member 84 ensures that the seal member ball 38 rolls off to the right in the drawing to an unseated position shown in phantom as the probe is inserted through the seat member opening 36.

Some forms of the probe inlet apparatus according to the invention may not include any offsetting means such as the offset ball 66 in FIGS. 2-5 and the offset pin 84 in FIG. 6. For example, a probe inlet apparatus according to the invention may include a seal member, such as the ball 38 in FIG. 2, alone in the ball container chamber defined by the frustoconical shaped guide surface 42 in that figure. This alternate form of the invention relies on the magnetic positioning force or the force of gravity to roll the seal member ball 38 to one side of the probe as it is inserted through the seat member opening.

Figure 7:
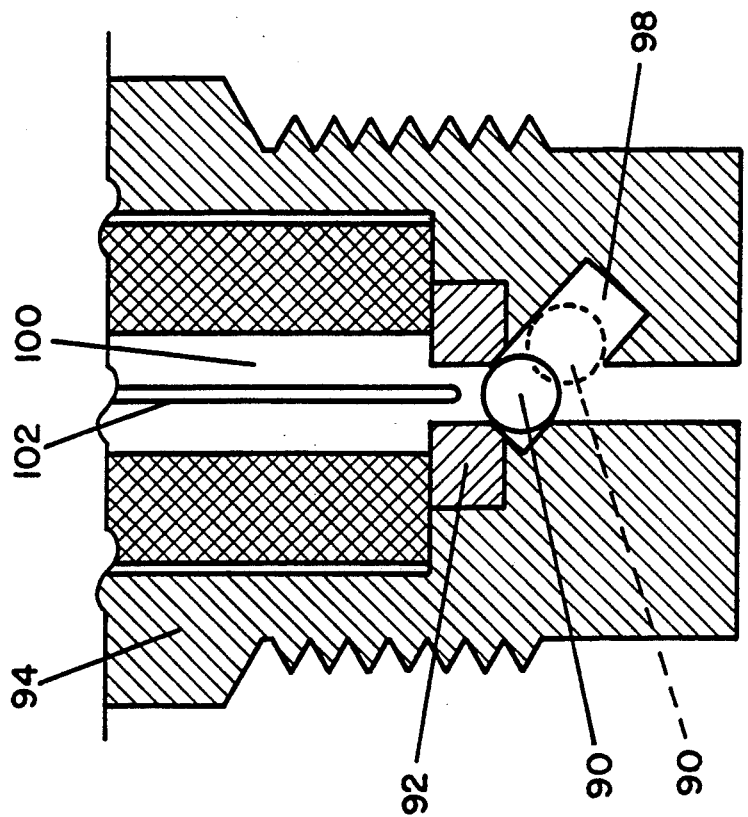
FIG. 7 is a partial section view showing a seal member guide channel according to the invention.

FIG. 7 shows another embodiment of the invention including an alternate seal member guide means. This embodiment includes a seal member or ball 90, similar to seal member 38 in FIGS. 2-5, adapted to seat against a seat member 92 similar to the seat member 34 shown in FIGS. 2-5. The seat member 92 is mounted in an inlet housing 94 along with an annular seal member (not shown) also similar to the embodiment shown in FIGS. 2-5. However, the ball 90 in FIG. 7 is received in a sealing member channel 98 extending at an angle over 90° and less than 180° from an inlet housing cavity 100 through which a probe 102 is inserted. The channel 98 serves as a guide means and offsetting means to offset the seal member 90 from its seated position so that the probe member 102 may pass as it is inserted through the inlet housing cavity 100, and to guide the seal member back to the seated position as the probe member is withdrawn. Similar to the embodiments shown in FIGS. 2-5, the seal member 90 in the embodiment shown in FIG. 7 is responsive to a magnetic positioning force produced by a magnet 104 that holds the seal member ball 90 in a seated position when the probe 102 is not received through the seat member, and returns the seal member to the seated position when the probe is withdrawn.

Although the channel 98 limits the displacement of the seal member 90 to one side of the probe member 102 unlike the frustoconical guide surface 42 in FIGS. 2-5, this limited transverse displacement direction does not introduce substantial lateral force on the probe member unlike prior probe inlet 13 devices. As in the embodiment shown in FIGS. 2-5, the magnetic positioning force on the seal member 90 does not increase as the probe member 102 displaces the seal member. Also, the initial contact between the probe member 102 and the spherical seal member 90 is substantially on-axis so that substantially no lateral force is placed on the probe member at such initial sealbreaking contact.

The above described preferred embodiments are intended to illustrate the principles of the invention, but not to limit the scope of the invention. Various other embodiments and modifications to these preferred embodiments may be made by those skilled in the art without departing from the scope of the following claims.

I claim:

1. A probe inlet apparatus for facilitating the introduction of an elongated probe member into an isolated environment, the inlet apparatus comprising:
   (a) an inlet housing having an inlet housing cavity extending therethrough through which the elongated probe member may pass;
   (b) annular seal means connected to the inlet housing for providing an annular seal around the probe member so that fluid may not flow through the inlet housing cavity when the probe member is received through said cavity;
   (c) an inner seal seat mounted toward an inner end of the inlet housing from the annular seal means, the inner seal seat having a seat opening through which the probe member may pass when the probe member is extended completely through the inlet housing cavity;
   (d) seal member positioning means associated with the inlet housing for providing a magnetic positioning force; and
   (e) a seal member responsive to the magnetic positioning force to be positioned in a seated position against the inner seal seat over the seat opening for preventing fluid from flowing through the inlet housing cavity from the seal opening toward the annular seal means, and adapted to be contacted and moved to an unseated position against said magnetic positioning force by the probe member as the probe member is inserted through the seat opening toward the inner end of the inlet housing from the annular seal means.

2. The probe inlet apparatus of claim 1 wherein the seal member is held in the seated position such that the initial contact between the probe member and the seal member as the probe member is inserted through the inlet housing is at a surface on the seal member that is approximately perpendicular to the probe member so that substantially no lateral force is exerted on the probe member upon such initial contact.

3. The probe inlet apparatus of claim 2 including:
   (a) seal member guide means mounted within the inlet housing for guiding the seat member from the unseated to the seated position when the probe member is withdrawn from the inlet housing.

4. The probe inlet apparatus of claim 3 wherein the seat member guide means comprises:
   (a) a generally frustoconical surface formed within the inlet housing with the smaller diameter end of the frustoconical shape positioned adjacent to the inner seal seat and with the shape increasing in diameter away from the inner seal seat toward the inner end of the inlet housing.

5. The probe inlet apparatus of claim 4 including:
   (a) seal member containing means connected over the larger diameter end of the frustoconical surface for containing the seal member within the area of the frustoconical shape while allowing the probe member to be inserted past the area of the frustoconical shape.

6. The probe inlet apparatus of claim 5 including:
   (a) offsetting means positioned in the area of the frustoconical shape for contacting the seal member after it is unseated by the probe member so as to offset the seal member to one side of the probe member as the probe member is inserted further through the seat opening.

7. The probe inlet apparatus of claim 6 wherein:
   (a) the seal member is spherical in shape; and
   (b) the offsetting means includes an offsetting ball substantially identical to the seal member.

8. The probe inlet apparatus of claim 7 where the inner seal seat comprises a ring of temperature stable material.

9. The probe inlet apparatus of claim 3 wherein the seal member guide means comprises an elongated guide channel formed in the inlet housing having a longitudinal axis extending at an angle of more than 90° and less than 180° to a central longitudinal axis of the inlet housing cavity.

10. The probe inlet apparatus of claim 2 wherein the annular seal means includes:
    (a) an annular seal member adapted to be mounted in the inlet housing cavity at an outer end of the inlet housing with an annular seal opening substantially axially aligned with the seat opening of the inner seal seat member; and
    (b) annular seal member retainer means for retaining and sealing the annular seal member within the inlet housing cavity of the inlet housing.

11. The probe inlet apparatus of claim 10 wherein:
    (a) the annular seal member includes a positioning flange adapted to abut the outer end of the inlet housing when the annular seal member is mounted in the inlet housing; and
    (b) the annular seal member retainer means includes a retainer connector member adapted to connect to the inlet housing over the outer end thereof so as to press the positioning flange of the annular seal member tightly against the inlet housing outer end to form a seal there between.

12. The probe inlet apparatus of claim 10 wherein the seal member positioning means comprises a permanent magnet having a magnet opening extending longitudinally therethrough mounted within the inlet housing between the annular seal means and the inner seal seat member with the magnet opening generally axially aligned with the inner seal opening and the annular seal opening through the annular seal member.

13. A probe inlet apparatus for facilitating the introduction of an elongated probe member into an isolated environment, the inlet apparatus comprising:
    (a) a seat member having a seat member opening into the isolated environment;
    (b) annular seal means for receiving the probe member and forming an annular seal around the probe member when the probe member is received therethrough;
    (c) an inlet housing connected to the inlet seat member and the annular seal means so as to form an inlet chamber having an inlet housing cavity extending between the seat member opening and the annular seal means;
    (d) a seal member container chamber connected to the inlet housing adjacent to the seat member and on the opposite side of the seat member from the inlet chamber;

(e) seal member positioning means associated with the inlet housing for providing a magnetic positioning force; and (f) a seal member contained in the seal member container chamber and being responsive to a magnetic positioning force to be positioned in a seated position against the seat member to form an inner seal, the seal member also being adapted to be contacted and moved to an unseated position against the magnetic positioning force by the probe member as the probe member is inserted through the seat member opening from the inlet chamber to the seal member container chamber.

14. The probe inlet apparatus of claim 13 wherein the seal member is held in the seated position such that the initial contact between the probe member and the seal member as the probe member is inserted through the inlet housing is at a surface on the seal member that is approximately perpendicular to the probe member so that substantially no lateral force is exerted on the probe member upon such initial contact.

15. The probe inlet apparatus of claim 13 including:
(a) offsetting means positioned in the seal member container chamber for contacting the seal member after it is unseated by the probe member so as to offset the seal member to one side of the probe member as the probe member is inserted further through the seat member opening.

16. The probe inlet apparatus of claim 15 wherein:
(a) the seal member is spherical in shape; and
(b) the offsetting means includes an offsetting ball substantially identical to the seal member.

17. A method of introducing an elongated probe member into an isolated environment comprising the steps of:
(a) retaining a seal member in a seated position over a seat member opening so as to form an inner seal to the isolated environment;
(b) inserting a forward end of the probe member through an annular seal member connected with a seat member through which the seat member opening is formed to form an annular seal around the probe member and a substantially sealed chamber between the inner seal and the annular seal;
(c) inserting the forward end of the probe further through the annular seal and through the seat member opening so as to contact and move the seal member to an unseated position while continuously maintaining the annular seal around the probe member, the forward end of the probe member being exposed to the isolated environment when the seal member is in the unseated
(d) withdrawing the probe member from the seat member opening while maintaining the annular seal;
(e) positioning the seal member back in the seated position over the seat member opening with a magnetic seal member positioning force to reestablish the inner seal while maintaining the annular seal; and
(f) withdrawing the probe member from the annular seal member.

18. The method of claim 17 wherein the step of inserting the probe further to unseat the seal member includes:
(a) displacing the seal, member in a direction transverse to a central longitudinal probe axis.

19. The method of claim 18 wherein the step of displacing the seal member includes:
(a) contacting the seal member after it is unseated with an offsetting member.

20. The method of claim 19 wherein the step of positioning the seal member back in the seated position includes:
(a) guiding the seal member toward the seat member opening with a guide surface extending radially away from the seat opening with respect to a central longitudinal axis of the seat member opening at an angle to said axis of more than 90° and less than 180°.

21. The method of claim 18 including the step of:
(a) dampening movement of the seal member in a direction transverse to the probe axis when the probe member is withdrawn from the seat member opening.

* * * * *